(12) United States Patent
Bestebreurtje

(10) Patent No.: US 7,726,191 B2
(45) Date of Patent: Jun. 1, 2010

(54) METHOD AND APPARATUS FOR ULTRASONIC TESTING OF AN OBJECT

(75) Inventor: Pieter Bestebreurtje, Tiel (NL)

(73) Assignee: Sonimex B.V., Tiel (NL)

( * ) Notice: Subject to any disclaimer, the term of this patent is extended or adjusted under 35 U.S.C. 154(b) by 776 days.

(21) Appl. No.: 10/576,622

(22) PCT Filed: Oct. 19, 2004

(86) PCT No.: PCT/NL2004/000738

§ 371 (c)(1),
(2), (4) Date: Jan. 24, 2007

(87) PCT Pub. No.: WO2005/038448

PCT Pub. Date: Apr. 28, 2005

(65) Prior Publication Data
US 2007/0169554 A1 Jul. 26, 2007

(30) Foreign Application Priority Data
Oct. 22, 2003 (NL) .................................. 1024593

(51) Int. Cl.
*G01N 29/00* (2006.01)
(52) U.S. Cl. ............................. 73/614; 73/618; 73/622; 73/627; 73/636
(58) Field of Classification Search ............ 73/614, 73/615, 616, 618, 620, 622, 627, 636, 596
See application file for complete search history.

(56) References Cited

U.S. PATENT DOCUMENTS

| | | | |
|---|---|---|---|
| 3,962,908 A | 6/1976 | Joy | |
| 4,429,576 A | 2/1984 | Norris | |
| 4,457,178 A * | 7/1984 | Turbe et al. | 73/636 |
| 4,700,574 A | 10/1987 | Turbe | |
| 5,020,371 A | 6/1991 | Panetti | |
| 5,341,683 A * | 8/1994 | Searle | 73/597 |
| 5,419,196 A * | 5/1995 | Havira et al. | 73/636 |
| 5,574,224 A * | 11/1996 | Jaeggi | 73/636 |
| 6,055,862 A | 5/2000 | Martens | |
| 6,568,270 B2 * | 5/2003 | Hongerholt | 73/596 |

FOREIGN PATENT DOCUMENTS

| | | |
|---|---|---|
| JP | 2002005903 | 1/2002 |
| JP | 2002005904 | 1/2002 |
| WO | WO 82/03920 | 11/1982 |

* cited by examiner

*Primary Examiner*—J M Saint Surin
(74) *Attorney, Agent, or Firm*—Weingarten, Schurgin, Gagnebin & Lebovici LLP

(57) ABSTRACT

A method for ultrasonic testing of an object, wherein at least one test moment an ultrasonic test signal (S1, S2) is transmitted into the object (2), while after a particular verification period ($\Delta t_1$, $\Delta t_2$) measured from said test moment, an ultrasonic verification signal (S1', S2') is transmitted into the object (2), a possible echo of said test signal (S1, S2) being received from said object (2) at a particular first measuring moment, the possible echo being accepted as being the echo (E1, E2) of said test signal (S1, S2) only when the echo (E1', E2') of the verification signal is received at a particular second measuring moment. In addition, the invention provides an apparatus, evidently intended and designed for carrying out such a method and a use of such an apparatus.

24 Claims, 2 Drawing Sheets

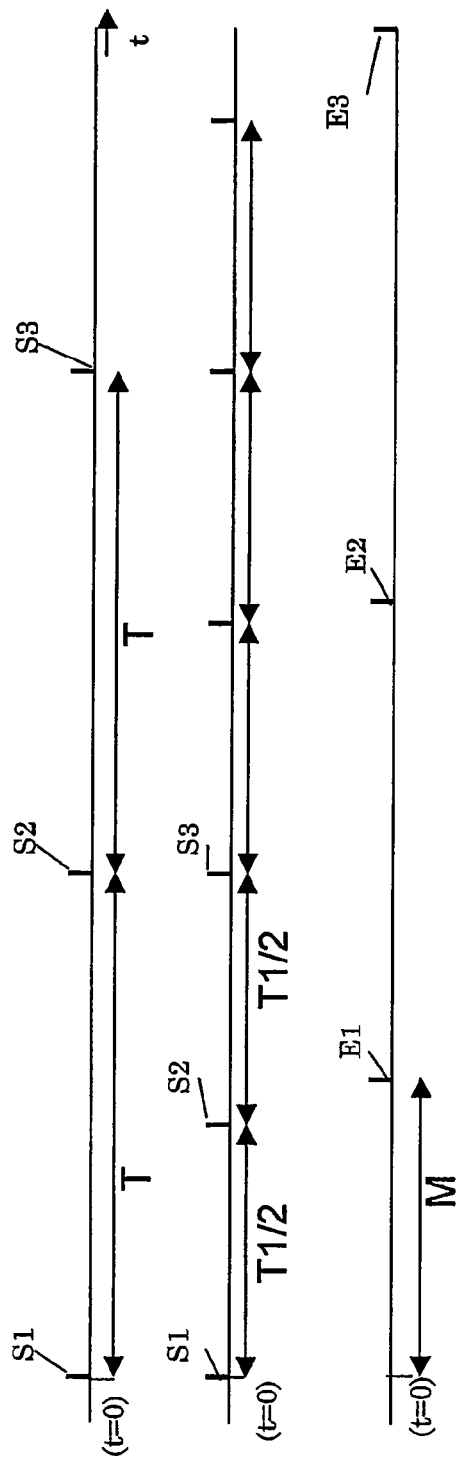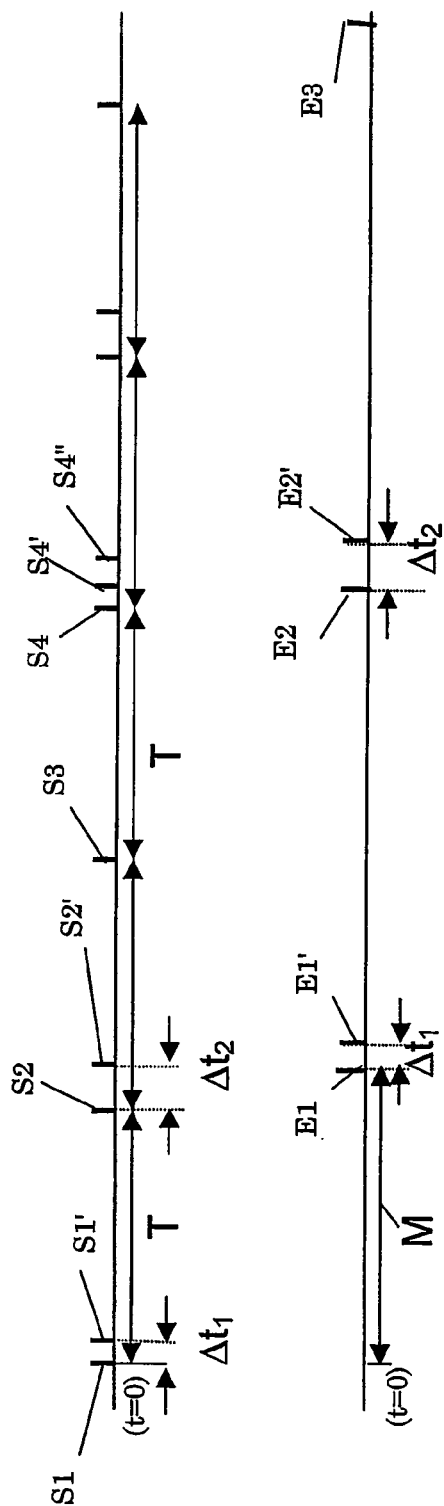

METHOD AND APPARATUS FOR ULTRASONIC TESTING OF AN OBJECT

Figure 5:
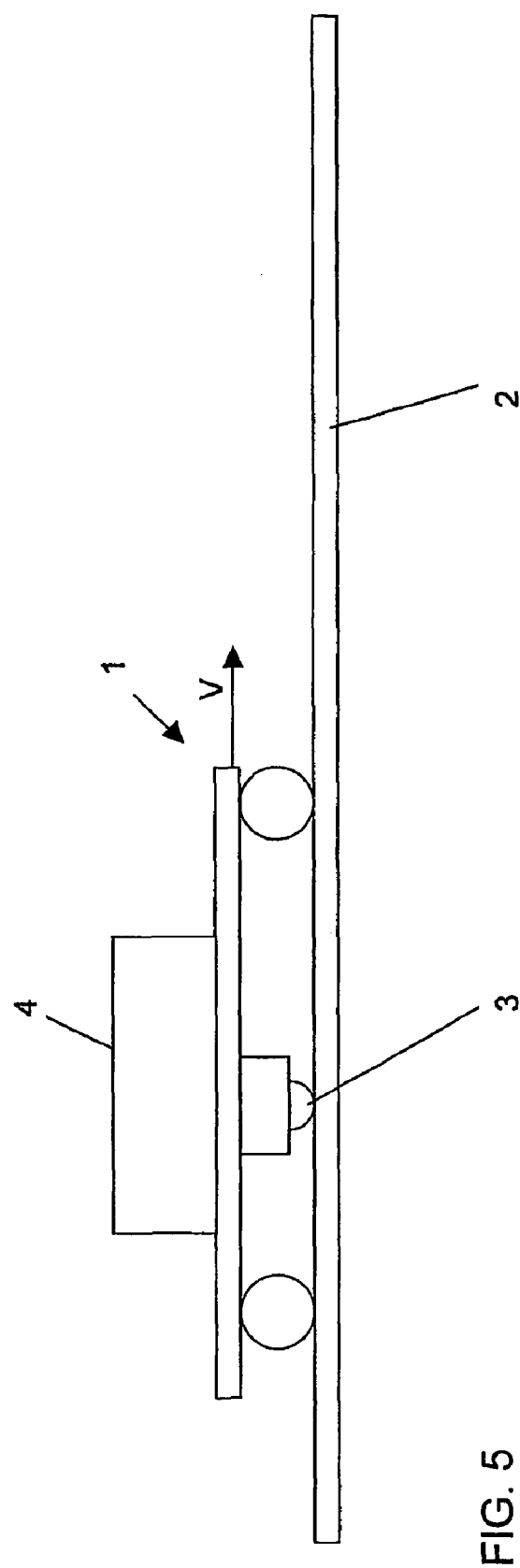

This application is a §371 national phase filing of PCT/NL2004/000738 filed Oct. 19, 2004, and claims priority to Dutch application No. 1024593 filed Oct. 22, 2003.

The invention relates to a method for ultrasonic testing of an object, wherein at least one moment of testing, an ultrasonic test signal is transmitted into the object.

Such a method is known per se from practice for detecting defects present in the object, for measuring the thickness of the object or the like, see for instance U.S. Pat. No. 6,055,862. The method is for instance suitable for detecting defects in train rails and/or wear of the train rails. A measuring train is then driven over the rails at a particular measuring velocity. The measuring train is provided with a number of transducers designed for transmitting ultrasonic test pulses perpendicularly and at specific angles into the rails. Moreover, the train is provided with detectors for receiving echoes coming from the test pulses. On the basis of the echo pattern delivered by these echoes, it can be determined whether defects are present in the rails, what the positions of the found defects are, and what the track height is. Determining this is, generally, carried out by suitable signal processing electronics, in particular one or more appropriately programmed computers. An advantage of the known method is that with it, an object can be checked for defects in a rapid and non-destructive manner.

A drawback of the known method is that it is relatively difficult to detect the associated echo of each sound signal transmitted into the object. For instance, different interference signals having a different source than the test signals can propagate through the object. When measurements are performed on rails, these interference signals can comprise, for instance, noise produced by the measuring train itself, for instance noise formed by the train wheels twisting when negotiating curves. Such interference signals can render the detection of the echo of a test signal impossible. In addition, the interference signals can be unintentionally detected as being echoes of the test signals, thereby leading to an incorrect test result.

Another source of disturbance of the measurement are the test signals themselves, in case the method is carried out with more than one test signal. In that case, it proves difficult to distinguish the echoes of the different test signals from each other, in particular when the test signal are successively transmitted along a part of the object to be tested in a relatively short period of time.

The object of the present invention is an improvement of the method for ultrasonic testing of an object. The object of the invention is in particular a method with which testing can be carried out relatively accurately.

To this end, the method according to the invention is characterized by the features of claim 1.

At least one test moment, an ultrasonic test signal is transmitted into the object. After a particular verification period, measured from the test moment, an ultrasonic verification signal is transmitted into the object. A possible echo of this test signal is received at a particular first measuring moment. This echo is accepted as being an echo of the test signal mentioned only when an echo of the verification signal is received at a second measuring moment. In this manner, the object can be ultrasonically tested particularly accurately. On the basis of the verification signal, it is then determined whether an ultrasonic signal received from the object actually is an echo of the test signal. If a received signal does not come from a test signal, often, no echo of a verification signal will be received. In that case, the received signal can be rejected. Possible echoes of test signals are accepted after receipt of associated echoes of verification signals only. With this method, interference signals can be separated well from test signals.

Acceptance of the test signal can also be considered as acceptance of receipt of the verification signal. In that case, the echo of the test signal serves to verify an echo of a verification signal emitted later. The parts of verification signal and test signal are then reversed.

According to the invention, the method can therefore be carried out in an equivalent manner, by first transmitting a verification signal into the object and then a test signal. The invention is then characterized in particular in that at least one test moment, an ultrasonic verification signal is transmitted into the object, while after a particular verification period, measured from the test moment mentioned, an ultrasonic test signal is transmitted into the object while a possible echo from this test signal is received from the object at a particular second measuring moment, the possible echo being accepted as being the echo of the test signal only when an echo of the verification signal is received at a particular first measuring moment.

This method, set forth in claim 2, utilizes the same inventive concept as the method according to claim 1 and therefore also offers the above-mentioned advantages.

According to a preferred embodiment, the alleged echo of the test signal mentioned is accepted as being the echo of this test signal only when the difference between the first and second measuring moment is substantially equal to the verification period mentioned.

Each test signal and an associated verification signal have been transmitted into the object with a particular intermediate verification period. When, thereupon, echoes having substantially the same intermediate verification period are received from the object, these echoes can be accepted as being the echoes of this test signal and this verification signal. By means of the verification period, the echo of the verification signal then proves that a particular echo belongs to a particular test signal.

The invention further provides an apparatus which is characterized by the subject matter of claim 9.

With this apparatus, the method according to the invention can be carried out in an advantageous manner, which offers the above-mentioned advantages. The apparatus can be used in different manners, for instance for testing objects, elements, rails, vehicle parts, vessel and/or airplane parts or the like.

Further elaborations of the invention are described in the subclaims. Presently, the invention will be further elucidated with reference to an exemplary embodiment and the drawing. In the drawing:

FIG. 1A schematically shows a time line of a method known from the state of the art, wherein a number of test signals are periodically transmitted into the object;

FIG. 1B shows a similar time line as FIG. 1A, the test signals being transmitted into the object with a halved period;

FIG. 2 schematically shows an echo pattern, belonging to the method represented in FIGS. 1A and 1B;

FIG. 3 schematically shows a time line of a method according to the present invention;

FIG. 4 schematically shows an echo pattern, belonging to the method represented in FIG. 3; and FIG. 5 shows an apparatus for carrying out a method for ultrasonic testing of an object.

FIGS. 1 and 2 schematically show a method known from practice wherein a number of ultrasonic pulses are periodically transmitted into an object. The method is carried out with, for instance, the measuring apparatus 1 schematically represented in FIG. 5. The measuring apparatus 1, for instance a part of a measuring train, is moveable over the object 2, for instance rails. The apparatus 1 is provided with a measuring and detecting system 3 which is designed for introducing ultrasonic pulses into the object 2 and receiving echoes coming from those pulses. The system 3 mentioned can be suitably brought into contact with the object 2, for instance directly or indirectly, via a liquid, via air or in a different manner. The measuring and detecting system 3 comprises one or more transducers (not shown) for generating the ultrasonic pulses and introducing them into the object, and one or more detectors (not shown) for receiving echoes of the ultrasonic pulses. The measuring and detecting system 3 is connected to a control 4 designed for processing signals received by the detectors. Preferably, the control is designed for determining from a received echo pattern, whether and where possible errors, breakages, defects and other irregularities are present in the object. In addition, the control is designed for, for instance, determining the thickness of the object on the basis of the echoes mentioned. Such a measuring apparatus 1 is known per se from practice, see for instance U.S. Pat. No. 6,055,862.

During use, the measuring apparatus 1 transmits a number of test signals into the object 1, for instance according to the test pattern represented in FIGS. 1A and 1B. FIG. 1 shows a time line along which a number of ultrasonic pulses have been indicated with reference numerals S1, S2, S3. The pulses S1, S2, S3 all have the same frequency spectrum and the same pulse duration. In the present exemplary embodiment, the pulses S1, S2, S3 are successively transmitted into the object 2 with a substantially fixed test period T from the moment t=0. Therefore, the first pulse S1 is transmitted at a first test moment t=0, the second pulse S2 at second test moment t=T and the third pulse S3 at a third test moment t=2T. When the measuring apparatus 1 is moved along the object 2 at a particular measuring velocity V, the pulses S1, S2, S3 will be introduced into the object 2 at substantially fixed mutual distances. Upon an increase of the measuring velocity V, for instance a doubling, the test period is to be reduced, for instance halved, for transmission of the pulses S1, S2, S3 into the object at the same distances, which is represented in FIG. 1B. For transmitting the pulses at desired distances into the object 2, the test period T can, for instance, comprise a particular measuring time and a particular waiting time. Naturally, during use, the test period T mentioned can also be varied in different manners. For instance, the test period can for instance be varied with a particular measuring velocity V of the measuring apparatus 1. In addition, the test period can for instance be adjusted to an acceleration and/or deceleration of the measuring apparatus 1. The measuring and detecting apparatus can for instance be coupled to a tachometer (not represented) of the apparatus 1.

Echo signals coming from the test pulses S1, S2, S3 are received by the measuring apparatus 1. The associated echo pattern with echoes E1, E2, E3 is represented in FIG. 2. The first echo E1, coming from the first test pulse S1, is received at a particular first measuring moment, following a measuring period M after the first test moment t=0. The length of this measuring period M depends inter alia on the sound velocity in the material of the object 2 to be tested and the dimensions of this object 2, and of the sound velocity of the materials and the substances present between the object 2 and the detectors of the apparatus 1. As follows from FIGS. 1B and 2, the echo E1 of the first pulse S1 can for instance arrive at the detector only after the second pulse S2 has been transmitted. In that case, the second pulse S2 can interfere with the receipt of the echo E1 of the first pulse. Moreover, this known method is sensitive to other interference signals propagating through the object 2.

FIGS. 3 and 4 schematically show time lines of an exemplary embodiment of a method according to the present invention which is relatively insensitive to interference signals. As shown in FIG. 3, several ultrasonic test signals S1, S2, S3, S4 are then transmitted into the object 2 at particular test moments, with an intermediate test period T. The test period T between neighbouring test signals S1, S2, S3, S4 is, for instance, less than approximately 1 ms, and is more in particular in the range of 0.5-0.01 ms. Naturally, the test period can also be approximately 1 ms or more, depending on the use and/or measuring velocity of the apparatus. The test periods T of the test signals S1, S2, S3, S4 can for instance be such that the test signals are transmitted into the object 2 approximately every one or few millimeters when the apparatus is moved along the object 2 at a particular velocity V. Preferably, during use, the apparatus 1 is moved along the object at a measuring velocity V which is greater than approximately 10 m/s, more in particular greater than approximately 20 m/s. As a result, a large part of the object can be tested relatively rapidly. It is, for instance, very advantageous when the measuring velocity V is at least approximately 30 m/s while the test signals are transmitted into the object every 2 to 3 mm.

With some of the test signals S1, S2 and S4, also, ultrasonic verification signals S1', S2', S4', S4" are transmitted into the object 2, in particular after particular verification periods $\Delta t_1$, $\Delta t_2$, measured from the test moments mentioned. In the exemplary embodiment, one verification signal S1' is transmitted one first verification period $\Delta t_1$ after the first test moment t=0. A verification signal S2' is transmitted after a second verification period $\Delta t_2$ from the second test moment t=T. In the exemplary embodiment, the second verification period $\Delta t_2$ is longer than the first verification period $\Delta t_1$ for distinguishing the associated echoes from each other. Two verification signals S4' and S4" are transmitted at suitable verification periods after the third test moment t=2T. In the exemplary embodiment, no verification signal is transmitted for the purpose of verifying the third test signal S3. Naturally, more test signals, with or without associated verification signals, can be introduced into the object 2. Further, verification signals can for instance also be transmitted prior to associated test signals, which has not been represented in the Figures. Moreover, the test periods T between the test signals can be greater than the verification period $\Delta t_1$, $\Delta t_2$ mentioned.

Preferably, each test signal S1, S2 and one or more associated verification signals S1', S2', are introduced close to each other into the object 2, so that echoes of these signals come from substantially the same part of the object 2, which renders the verification of the test signals extra accurate. Each test signal can, for instance, be transmitted into the object 2 at a first position, while an associated verification signal S1', S2' is transmitted into the object 2 at a second position adjacent said first position. Preferably, the distance between the first and second position is smaller than approximately 1 mm, and is in particular approximately 0.5 mm or less, more in particular approximately 0.1 mm or less.

Preferably, each verification period is relatively small with respect to the test period T of the test signals. For instance, the verification period $\Delta t_1$, $\Delta t_2$ is preferably smaller than approximately 100 μs, in particular smaller than approximately 50 μs, more in particular smaller than approximately 20 μs. The verification period can for instance be in the range of approximately 1-20 μs. When different verification periods $\Delta t_1$, $\Delta t_2$ are used, as is the case in the exemplary embodiment, these can differ from each other by, for instance, one or a few μs. One verification period can for instance take longer than approximately 10 μs, while, conversely, the other is shorter.

FIG. 4 shows a part of the echo pattern of the test pattern represented in FIG. 3, following a good receipt of the echoes E1, E2, E1', E2' coming from the test signals S1, S2 and verification signals S1', S2'. Here, each echo of each test signal is received at a first associated measuring moment. In the exemplary embodiment, the received echo E1, E2 of each test signal S1, S2 is verified on the basis of the receipt, and in particular the moment of receipt of the echo E1', E2' of the associated verification signal S1', S2'. The echo of each test signal S1, S2 is accepted only when the echo E1', E2' of the associated verification signal S1', S2' is received at a particular second measuring moment and when the difference between the first and second measuring moment is substantially equal to the verification period mentioned. The fact is that, at least with the present exemplary embodiment, upon a proper receipt, the verification echo is received approximately an associated verification period later than the echo of the associated test signal. In case a verification signal is transmitted prior to an associated test signal, upon a correct receipt, the verification echo is received approximately an associated verification period sooner than the echo of the associated test signal. When no verification signal is received or at a different moment than the expected moment, a received, associated, alleged echo of a test signal is rejected.

Preferably, test signals and verification signals are used which are substantially equal to each other, which renders measuring and signal processing thereof relatively accurate. In particular each test signal and each associated verification signal have substantially the same signal duration, substantially the same amplitude and substantially the same frequency spectrum so that an accurate verification can be carried out. On the other hand, each test signal and verification signal can for instance differ from each other as to, for instance, signal duration, amplitude and/or frequency spectrum. Further, the test signals can mutually be the same or differ as to pulse duration, amplitude and/or frequency.

In order to carry out the present invention, the invention further provides an apparatus which is preferably provided with a control, in particular computer means, which control is designed for accepting an echo received at a particular measuring moment as being an echo E1, E2 of a test signal S1, S2 only when an echo E1', E2' of the verification signal S1', S2' is received at a particular different measuring moment. Preferably, the control is then designed for accepting a received echo only when the difference between the one and other measuring moment is substantially equal to the verification period $\Delta t_1$, $\Delta t_2$ mentioned, which renders the apparatus particularly accurate and insensitive to interference signals.

It is self-evident that the invention is not limited to the exemplary embodiment described. Various modifications are possible within the framework of the invention as set forth in the following claims.

For instance the transducers, detectors and such can be designed and arranged in various manners. The measuring apparatus 1 can further be designed in different manners, which is for instance dependent on the object to be tested therewith.

Further, different test signals can for instance be distinguished from each other well when the length of the verification period is varied with a number of test signals to be successively transmitted. In addition, for instance, some test signals can be provided with verification signals and others not. Further, for the purpose of verification of a test signal, for instance several associated verification signals can be generated, with easily recognizable intermediate verification periods.

The test signals can comprise different signals, for instance signals with a relatively short pulse duration of a few μs or less. Furthermore, the signals can be transmitted perpendicularly to and/or at different angles into the object to be tested.

In addition, one or more verification signals can for instance be transmitted into the object prior to and/or after at least one test signal for verification of a possible echo of that test signal.

The invention claimed is:

1. A method for ultrasonic testing of an object, wherein at least one test moment an ultrasonic test signal (S1, S2) is transmitted into the object, while after a particular verification period ($\Delta t_1$, $\Delta t_2$) measured from said test moment, an ultrasonic verification signal (S1', S2') is transmitted into the object, a possible echo of said test signal (S1, S2) being received from said object at a particular first measuring moment, the possible echo being accepted as being the echo (E1, E2) of said test signal (S1, S2) only when an echo (E1', E2') of the verification signal (S1', S2') is received at a particular second measuring moment.

2. A method according to claim 1, wherein the possible echo of said test signal is accepted as being the echo (E1, E2) of that test signal (S1, S2) only when the difference between the first and the second measuring moment is substantially equal to said verification period ($\Delta t_1$, $\Delta t_2$).

3. A method according to claim 2, wherein:
said test signal (S1, S2) and each associated verification signal (S1', S2') are equal to each other and have in particular the same signal duration, the same amplitude and the same frequency spectrum;
said test signal (S1, S2) is transmitted into the object at a first position, while said verification signal (S1', S2') is transmitted into the object at a second position adjacent said first position;
the distance between the first and second position is smaller than approximately 1 mm, is in particular approximately 0.5 mm or less, more in particular approximately 0.1 mm or less;
said verification period ($\Delta t_1$, $\Delta t_2$) is smaller than approximately 100 μs, more in particular smaller than approximately 50 μs, more in particular smaller than approximately 20 μs;
successively a number of test signals (S1, S2, S3, S4) are transmitted into the object, in particular with intermediate test periods (T) which are greater than said verification period ($\Delta t_1$, $\Delta t_2$), while after and/or prior to at least one of said test signals, at least one associated verification signal (S1', S2', S4', S4") is transmitted into the object.

4. A method according to claim 1, wherein said test signal (S1, S2) and each associated verification signal (S1', S2') are equal to each other and have in particular the same signal duration, the same amplitude and the same frequency spectrum.

5. A method according to claim 1, wherein said test signal (S1, S2) is transmitted into the object at a first position, while said verification signal (S1', S2') is transmitted into the object at a second position adjacent said first position.

6. A method according to claim 5, wherein the distance between the first and second position is smaller than approximately 1 mm, is in particular approximately 0.5 mm or less, more in particular approximately 0.1 mm or less.

7. A method according to claim 1, wherein said verification period ($\Delta t_1$, $\Delta t_2$) is smaller than approximately 100 μs, more in particular smaller than approximately 50 µs, more in particular smaller than approximately 20 µs.

8. A method according to claim 1, wherein successively a number of test signals (S1, S2, S3, S4) are transmitted into the object, in particular with intermediate test periods (T) which are greater than said verification period ($\Delta t_1$, $\Delta t_2$), while after and/or prior to at least one of said test signals, at least one associated verification signal (S1', S2', S4', S4") is transmitted into the object.

9. An apparatus for carrying out the method according to claim 1.

10. An apparatus according to claim 9, wherein, during use, the apparatus is moved along the object at a particular measuring velocity (V), while the measuring velocity (V) is in particular greater than approximately 10 m/s and more in particular greater than approximately 20 m/s.

11. An apparatus according to claim 9, provided with a control, in particular computer means, which control is designed for accepting an echo received at a particular measuring moment as being an echo (E1, E2) of the test signal (S1, S2) only when an echo (E1', E2') of the verification signal (S1', S2') is received at a different measuring moment, and in particular when the difference between the one and other measuring moment is substantially equal to said verification period ($\Delta t_1$, $\Delta t_2$).

12. The use of an apparatus according to claim 9, in particular for testing objects, elements, rails, vehicle parts, vessel parts and/or airplane parts and the like for defects.

13. A method for ultrasonic testing of an object, wherein at least one test moment an ultrasonic verification signal (S1', S2') is transmitted into the object while after a particular verification period ($\Delta t_1$, $\Delta t_2$) measured from said test moment, an ultrasonic test signal (S1, S2) is transmitted into the object, a possible echo of said test signal (S1, S2) being received from said object at a particular second measuring moment, the possible echo being accepted as being the echo (E1, E2) of said test signal (S1, S2) only when an echo (E1', E2') of the verification signal (S1', S2') is received at a particular first measuring moment.

14. A method according to claim 2, wherein the possible echo of said test signal is accepted as being the echo (E1, E2) of that test signal (S1, S2) only when the difference between the first and the second measuring moment is substantially equal to said verification period ($\Delta t_1$, $\Delta t_2$).

15. A method according to claim 14, wherein:
said test signal (S1, S2) and each associated verification signal (S1', S2') are equal to each other and have in particular the same signal duration, the same amplitude and the same frequency spectrum;
said test signal (S1, S2) is transmitted into the object at a first position, while said verification signal (S1', S2') is transmitted into the object at a second position adjacent said first position;
the distance between the first and second position is smaller than approximately 1 mm, is in particular approximately 0.5 mm or less, more in particular approximately 0.1 mm or less;

said verification period ($\Delta t_1$, $\Delta t_2$) is smaller than approximately 100 µs, more in particular smaller than approximately 50 µs, more in particular smaller than approximately 20 µs;
successively a number of test signals (S1, S2, S3, S4) are transmitted into the object, in particular with intermediate test periods (T) which are greater than said verification period ($\Delta t_1$, $\Delta t_2$), while after and/or prior to at least one of said test signals, at least one associated verification signal (S1', S2', S4', S4") is transmitted into the object.

16. A method according to claim 2, wherein said test signal (S1, S2) and each associated verification signal (S1', S2') are equal to each other and have in particular the same signal duration, the same amplitude and the same frequency spectrum.

17. A method according to claim 2, wherein said test signal (S1, S2) is transmitted into the object at a first position, while said verification signal (S1', S2') is transmitted into the object at a second position adjacent said first position.

18. A method according to claim 17, wherein the distance between the first and second position is smaller than approximately 1 mm, is in particular approximately 0.5 mm or less, more in particular approximately 0.1 mm or less.

19. A method according to claim 2, wherein said verification period ($\Delta t_1$, $\Delta t_2$) is smaller than approximately 100 µs, more in particular smaller than approximately 50 µs, more in particular smaller than approximately 20 µs.

20. A method according to claim 2, wherein successively a number of test signals (S1, S2, S3, S4) are transmitted into the object, in particular with intermediate test periods (T) which are greater than said verification period ($\Delta t_1$, $\Delta t_2$), while after and/or prior to at least one of said test signals, at least one associated verification signal (S1', S2', S4', S4") is transmitted into the object.

21. An apparatus for carrying out the method according to claim 2.

22. An apparatus according to claim 21, wherein, during use, the apparatus is moved along the object at a particular measuring velocity (V), while the measuring velocity (V) is in particular greater than approximately 10 m/s and more in particular greater than approximately 20 m/s.

23. An apparatus according to claim 21, provided with a control, in particular computer means, which control is designed for accepting an echo received at a particular measuring moment as being an echo (E1, E2) of the test signal (S1, S2) only when an echo (E1', E2') of the verification signal (S1', S2') is received at a different measuring moment, and in particular when the difference between the one and other measuring moment is substantially equal to said verification period ($\Delta t_1$, $\Delta t_2$).

24. The use of an apparatus according to claim 21, in particular for testing objects, elements, rails, vehicle parts, vessel parts and/or airplane parts and the like for defects.

* * * * *

UNITED STATES PATENT AND TRADEMARK OFFICE
CERTIFICATE OF CORRECTION

PATENT NO. : 7,726,191 B2  
APPLICATION NO. : 10/576622  
DATED : June 1, 2010  
INVENTOR(S) : Pieter Bestebreurtje Page 1 of 1

It is certified that error appears in the above-identified patent and that said Letters Patent is hereby corrected as shown below:

Column 7, claim 14, line 40, "2" should read --13--;

Column 8, claim 16, line 12, "2" should read --13--;

Column 8, claim 17, line 17, "2" should read --13--;

Column 8, claim 19, line 25, "2" should read --13--;

Column 8, claim 20, line 29, "2" should read --13--; and

Column 8, claim 21, line 37, "2" should read --13--.

Signed and Sealed this  
Eighth Day of February, 2011

David J. Kappos  
*Director of the United States Patent and Trademark Office*